United States Patent [19]

Kostusyk et al.

[11] Patent Number: 4,753,745

[45] Date of Patent: Jun. 28, 1988

[54] METHYLENE LINKED AROMATIC POUR POINT DEPRESSANT

[75] Inventors: Joseph L. Kostusyk, Euclid; Syed Q. A. Rizvi, Painesville, both of Ohio

[73] Assignee: The Lubrizol Corporation, Wickliffe, Ohio

[21] Appl. No.: 814,692

[22] Filed: Dec. 30, 1985

[51] Int. Cl.$^4$ ................ C10M 131/06; C10M 147/02
[52] U.S. Cl. ......................................... 252/58; 44/62; 44/79; 570/183; 570/184; 570/199; 570/210; 585/1; 585/11; 585/25
[58] Field of Search .............. 252/58; 44/62; 570/183, 570/184, 199, 210; 585/407, 415, 417

[56] References Cited

U.S. PATENT DOCUMENTS

| | | | |
|---|---|---|---|
| 1,667,214 | 4/1928 | Michel | 585/26 |
| 1,815,022 | 7/1931 | Davis | 585/8 |
| 3,883,318 | 5/1975 | Feldman et al. | 44/62 |
| 3,910,776 | 10/1975 | Feldman | 44/62 |
| 4,255,159 | 3/1981 | Miller et al. | 44/62 |

FOREIGN PATENT DOCUMENTS 715045 12/1941 Fed. Rep. of Germany ......... 39 C/

*Primary Examiner*—Steven Capella
*Assistant Examiner*—Ellen McAvoy

*Attorney, Agent, or Firm*—Karl Bozicevic; Denis A. Polyn; Robert A. Franks

[57] ABSTRACT

Compositions useful as pour point depressants, novel compounds within such compositions, and processes for making same, as well as lubricant oil compositions containing same, are disclosed. The novel compounds are encompassed by the general structural formula (I)

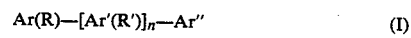

$$Ar(R)-[Ar'(R')]_n-Ar'' \qquad (I)$$

wherein the Ar, Ar' and Ar" are independently an aromatic moiety containing 1 to 3 aromatic rings and each aromatic moiety is substituted with 0 to 3 substituents, (R) and (R') are independently an alkylene group containing about 1 to 100 carbon atoms with the proviso that at least one of (R) or (R') is CH$_2$, and n is 0 to about 1000; with the proviso that if n is 0, then (R) is CH$_2$ and each aromatic moiety is independently substituted with 0 to 3 substituents with one aromatic moiety having at least one substituent, the substituents being selected from the group consisting of a substituent derived from an olefin and a substituent derived from a chlorinated hydrocarbon. The composition of the invention includes compounds varying in molecular weight from about 271 to about 300,000.

18 Claims, No Drawings

METHYLENE LINKED AROMATIC POUR POINT DEPRESSANT

FIELD OF THE INVENTION

This invention relates to the field of hydrocarbon oil additives and more particularly to novel pour point depressant compositions, novel compounds within such compositions, processes for making same, concentrates, fuel oils, oils of lubricating viscosity, automatic transmission fluids, gear oils, hydraulic oils, crude oils and residual oils containing same.

BACKGROUND OF THE INVENTION

Various types of distillate fuel oils such as diesel fuels, various oils of lubricating viscosity, automatic transmission fluids, hydraulic oil, home heating oils, and crude oils require the use of pour point depressant additives in order to allow them to flow freely at lower temperatures. The use of such additives has been known for some time. For example, U.S. Pat. No. 1,667,214 to Michel discloses the use of a fuel additive which includes a mono-alkyl-naphthalene and a poly-alkyl-naphthalene. The additives disclosed within the patent are produced by alkylating naphthalene in the presence of an aluminum chloride catalyst.

U.S. Pat. No. 1,815,022 to Davis discloses a similar additive which is comprised of naphthalene substituted with a chlorinated wax. The chlorinated wax is added to the naphthalene in the presence of an aluminum chloride catalyst.

The pour point depressants, as disclosed by Michel and Davis, were utilized in oils which included higher amounts of kerosene than is normally present in such oils today. Kerosene acts as a solvent for the wax present in distillate fuel oils. However, demands for kerosene for use in jet fuels has caused the amount of kerosene present in distillate fuel oils to be decreased over the years. This, in turn, has required the addition of wax crystal modifiers which are increasingly efficient in order to make up for the lack of the kerosene.

An additive combination for cold flow improvement of distillate fuel oils is disclosed within U.S. Pat. No. 3,910,776 to Feldman. The combination includes alkyl aromatics which are the condensation product of a chlorinated wax and naphthalene with an ethylene-containing polymer and an N-aliphatic hydrocarbyl succinimic acid.

U.S. Pat. No. 3,883,318 to Feldman, et al. discloses another pour point depressant which is comprised of a mixture of compounds such as a hydrogenated wax aromatic pour point depressant, a hydrogenated alkyl aromatic fraction of an amorphous normal solid wax and an ethylene backbone pour point depressant.

U.S. Pat. No. 4,255,159 to Miller, et al. contains the disclosure of an additive which is a mixture of different types of cold flow property improving compounds. The additive is disclosed as having synergistic flow and filterability improving properties with respect to fuel oils. The additive may be comprised of:

(1) a polymer of isomerized monoolefins or the alkylation product of naphthalene with the polymeric monoolefin, and (2) the condensation product of a chlorinated paraffin and an aromatic hydrocarbon which may also be naphthalene.

This combination of two different types of substituted naphthalene compounds used as a fuel additive is indicated as having synergistic effects with respect to improving the cold flow and filterability properties of present day fuel oils.

SUMMARY OF THE INVENTION

A class of additives which act as pour point depressants, concentrates and oils containing same and methods of making same are disclosed. The additive compositions of the present invention include a large number of different compounds, some of which are novel compounds. Compounds in the compositions of the present invention have an extremely wide range of molecular weights. The compositions aid in improving the cold flow and filterability of present day oils such as lubricating oils, diesel fuel oils, crudes and heating oils. The novel compounds of the invention can be generally described by the general structural formula (I) as follows:

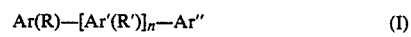

$$Ar(R)-[Ar'(R')]_n-Ar'' \qquad (I)$$

wherein the Ar, Ar' and Ar" are independently an aromatic moiety containing 1 to 3 aromatic rings and each aromatic moiety is substituted with 0 to 3 substituents (the aromatic rings are preferably benzene rings which may be linked but are preferably fused). (R) and (R') are independently an alkylene group containing 1 to 100 carbon atoms with the proviso that at least one of (R) or (R') is $CH_2$, and n is 0 to about 1000 or more; with the proviso that if n is 0, then (R) is $CH_2$ and each aromatic moiety is independently substituted with 0 to 3 substituents, with at least one aromatic moiety having at least one substituent, the substituents being selected from the group consisting of a substituent derived from an olefin (preferably an olefin containing 8 to 30 carbon atoms) and a substituent derived from a chlorinated hydrocarbon (preferably a chlorinated hydrocarbon containing 18 to 50 carbon atoms).

The "alkylene" linking groups (R) and (R') are substantially hydrocarbyl which may be a saturated hydrocarbon, e.g., methylene $CH_2$, ethylene $C_2H_4$; hydrocarbons containing unsaturated positions, i.e., alkenyls; and such saturated and unsaturated hydrocarbons substituted with chlorine. The term "alkylene" as used in the claims covers the above.

The novel composition which includes the novel compounds of the present invention are produced by a process comprising the steps of:

(a) providing aromatic compounds containing 1 to 3 aromatic rings, which compounds are precursors for aromatic moieties Ar, Ar' and Ar" in a reactor;

(b) adding a FRIEDEL-CRAFTS or Lewis Acid catalyst to the reactor;

(c) adding a chlorinated hydrocarbon to the reactor;

(d) adding an olefin to the reactor; and (e) adding $CH_2Cl_2$ to the reactor wherein step (e) is carried out concurrently with or prior to at least one of steps (a)–(d).

It is a primary object of the present invention to provide a novel class of compositions which when added to a hydrocarbon oil in relatively small amounts will act as pour point depressants.

A feature of the present invention is that the novel compositions of the invention can be added to hydrocarbon oil by themselves, without the addition of other pour point depressants, in order to obtain greatly improved cold flow and filtering properties.

Another feature of the present invention is that the compounds in the novel composition have molecular weights over a very wide range.

An advantage of the present invention is that it can be easily and economically manufactured and added to a lubricant to act as a pour point depressant without the need for other pour point depressant additives.

These and other objects, features and advantages of the present invention will become apparent to those skilled in the art upon reading the present disclosure.

DETAILED DESCRIPTION OF THE INVENTION

The novel pour point depressant compounds of the present invention can be described by the general structural formula (I):

$$Ar(R)-[Ar'(R')]_n-Ar'' \quad (I)$$

wherein the Ar, Ar' and Ar" are independently an aromatic containing 1 to 3 aromatic rings and each aromatic moiety is substituted with 0 to 3 substituents (the rings are preferably fused benzene rings), (R) and (R') are independently an alkylene group containing 1 to 100 carbon atoms with the proviso that at least one of (R) or (R') is CH$_2$, and n is 0 to about 1000 with the proviso that if n is 0, then (R) is CH$_2$ and each aromatic moiety is independently substituted with 0 to 3 substituents, with at least one aromatic moiety having at least one substituent, the substituents being selected from the group consisting of a substituent derived from an olefin (preferably an olefin containing 8 to 30 carbon atoms, more preferably 16-18 carbon atoms) and a substituent derived from a chlorinated hydrocarbon preferably containing 8 to 50 carbon atoms more preferably containing about 24 carbon atoms and about 2.5 chlorine atoms for each 24 carbon atoms.

The compositions of the present invention would include at least some novel compounds encompassed by the general structural formula (I) put forth above. It is not possible to readily determine what percentage of these novel compounds would be present in the composition.

The compositions of the present invention might include compounds having a molecular weight ranging from about 300 to 2,000, but preferably contains compounds ranging in molecular weight from about 500 to about 10,000 and most preferably contains compounds over an even broader molecular weight range of about 271 to about 300,000. A composition containing compounds over a broader molecular weight range results in better pour point depressant properties.

Compounds in the composition of the invention are likely to be encompassed by a more broadly defined general structural formula (II):

$$Ar(R)-[-Ar'(R')]_n Ar'' \quad (II)$$

wherein the Ar, Ar' and Ar" are independently an aromatic moiety and each aromatic moiety is substituted with 0 to 3 substituents (the preferred aromatic precursor being naphthalene), R and R' are independently straight or branch chain alkylenes containing 1 to 100 carbons and n is 0 to 1000.

The composition of the invention would then include compounds such as alkylated naphthalenes which are not novel, along with novel compounds of the present invention. The composition of the invention being characterized by the presence of compounds over a wide molecular weight range. The molecular weight of compounds in the composition of the invention could vary from that of a simple unsubstituted benzene to a polymer of 1000 monomers of trisubstituted naphthalenes linked by alkylenes containing as many as 100 carbon atoms with the substituents of the naphthalene containing 1 to 50 carbon atoms.

The substituents for the aromatic moieties of (I) or (II) are obtained from olefins and/or chlorinated hydrocarbons.

The useful olefins include 1-octene, 1-decene, and alpha-olefins of chain lengths $C_{12}$, $C_{14}$, $C_{16-18}$, $C_{15-20}$, $C_{20-24}$, $C_{24-28}$. More preferably the invention process is carried out with olefins which are mixtures of the above. A good example would be the $C_{15-20}$ cracked wax olefins, or a mixture of 1-octene and $C_{16-18}$ alpha olefin.

The chlorinated hydrocarbons might contain from 1-50 carbon atoms and from about 2 to about 84% chlorine by weight. Preferred chlorinated hydrocarbons are obtained by chlorinating slack waxes or paraffinic waxes of $C_{18-30}$ chain length so that they contain from 5-50% chlorine by weight. A particularly preferred chlorinated hydrocarbon, being one of about 24 carbons containing about 2.5 chlorines per 24 carbon atoms.

Although Ar, Ar' and Ar" may be any aromatic containing 1 to 3 aromatic rings, it is preferable if Ar, Ar' and Ar" are all the same. Further, it is preferable if Ar, Ar' and Ar" are fused benzene rings, i.e., when two or three benzene rings are present, the adjoining rings share two carbon atoms. Most preferably, Ar, Ar' and Ar" are all derived from naphthalene.

Aromatics which might be precursors of Ar, Ar' and Ar" include benzene, biphenyl, diphenylmethane, triphenylmethane, aniline, diphenylamine, diphenylether, phenol, naphthalene, anthracene and phenanthrene. Naphthalene is particularly preferred.

Although the aromatic groups of formula (I) above can contain 0 to 3 substituents, the composition will contain compounds with one or two substituents and will preferably include compounds with two substituents. The substituents may be derived from any olefin (preferably an alpha olefin containing 8 to 30 carbon atoms) or derived from a chlorinated hydrocarbon containing 8 to 50 carbon atoms (preferably a chlorinated hydrocarbon derived from a hydrocarbon wax containing 22-26 carbon atoms). In addition to or in place of forming the substituents, the olefin and/or chlorinated hydrocarbon may form the alkylene linking group (R and/or R' group) of the general structural formula (I). Compositions of the invention might include compounds wherein each of the naphthalene groups is substituted with one alkyl group containing 16 to 18 carbon atoms and one derived from a chlorinated hydrocarbon containing about 24 carbon atoms with about 2.5 chlorine atoms present for each 24 carbon atoms.

Any pour point depressant of the present invention would include a mixture of compounds encompassed by the general structural formula (I) as well as compounds not encompassed by (I) but encompassed by (II).

The desired material is a mixture of products which include alkylated naphthalenes, coupled and bridged naphthalenes, oligomers and dehydrohalogenated waxes. The mw distribution of the final product is a more useful characterization of the final product. A useful mw range is from 300-2000. A more useful mw range is from 500 to 10,000. A preferred distribution is from 400 to 112,000. The most useful distribution is from about 271 to about 300,000.

The compositions of the invention which include compounds of general formula (II) as well as novel compounds of general formula (I) are produced according to the following general process:

(a) providing aromatic compounds containing 1 to 3 aromatic rings which compounds are substituted with 0 to 3 substituents, the compounds being precursors for aromatic moieties Ar, Ar' and Ar" in a reactor;

(b) adding a FRIEDEL-CRAFTS or Lewis Acid catalyst to the reactor;

(c) adding a chlorinated hydrocarbon to the reactor;

(d) adding an olefin to the reactor and (e) adding $CH_2Cl_2$ to the reactor wherein step (e) is carried out prior to or concurrently with at least one step of (a)-(d).

As indicated above, the aromatic compounds forming Ar, Ar' and Ar" groups in the compound of the general formula are preferably naphthalene. If the aromatic compound is substituted, it is substituted with an alkyl or alkenyl, either of which may be chlorine substituted, branched or straight chain. Accordingly, in accordance with one embodiment of the process of the present invention, naphthalene is mixed with methylene chloride in a reaction flask. At this point, the methylene chloride acts as a solvent. A FRIEDEL-CRAFTS or Lewis Acid catalyst is then added to the mixture. The catalyst is preferably in the form of $AlCl_3$. After adding the catalyst, a chlorinated hydrocarbon (most preferably one containing 22-26 carbons) is added to the reaction flask and a reaction occurs between the naphthalene and the chlorinated hydrocarbon wax such that the napthalene is substituted with an alkyl group derived from the chlorinated hydrocarbon wax. Furthermore, linking will occur between naphthalene compounds via a methylene group as shown within general structural formula (I) when (R) or (R') is $CH_2$.

The mixture is then preferably cooled to a temperature in the range of 0° to 5° C. While continuing to cool the vessel, an olefin (preferably an alpha-olefin containing 8 to 30 carbon atoms) is added slowly so that the temperature is continually maintained in the range of 0° to 5° C. Alkylation of the naphthalene compounds occurs so that the naphthalenes are substituted with an alkyl group derived from said olefin. The catalyst is decomposed and is neutralized with a base such as lime after which stirring is continued while the temperature is raised first to 60° C. and then to 120° C. to remove the volatile components of the reaction mixture. The mixture is filtered and the desired product is isolated.

Chlorinated hydrocarbons which may form a substituent on one or more of the aromatic moieties may contain 1 to about 50 carbon atoms. If a chlorinated hydrocarbon containing 50 carbon atoms forms a substituent and is linked to another 50 carbon atom substituent on another aromatic moiety, the aromatic moieties will be linked by an alkylene containing 100 carbons, i.e., (R) or (R') is about 100 carbon atoms in general formula (I). However, the aromatic moieties Ar may be linked by a single $CH_2$, i.e., an alkylene containing a single carbon atom wherein (R) or (R') is $CH_2$.

The general process of the invention for producing the composition of general formula (I) can be carried out over a wide range of ratios of components. To describe the ratio of the components added in steps (a), (b), (c), (d) and (e) the components will be referred to respectively by the letters (a'), (b'), (c'), (d') and (e'). All that is necessary is that (e') be present in sufficient amount so that at least some methylene linking occurs between components (a') and/or that (b'), (c') and (d') be present in sufficient amounts so that there is at least some substitution of (a') by (c') and (d') as catalyzed by (b'). The components (a'), (b'), (c'), (d') and (e') might be present in weight ratios of (a'):(b'):(c'):(d'):(e') in the ranges of about (1):(0.01-1):(0.5-6):(0.5-22):(1-40) and most preferably (1):(0.2):(3):(11):(20); all ratios are in parts by weight.

The process can be carried out over a wide range of temperatures above the freezing point and up to the boiling points of the reaction mixture present at any point in steps (a)-(e). The boiling point of (e'), i.e., methylene chloride is about 40° C., however, the maximum reaction temperature may be higher or lower than 40° C. at atmospheric pressure due to the presence of other reactants. The process has been carried out at as low as −5° C. The reaction can also be carried out as subatmospheric or superatmospheric pressure.

The pour point depressant compositions of the present invention may be sold by itself or in concentrates, in combination with any other known additive which includes, but is not limited to dispersants, detergents, antioxidants, antiwear agents, extreme pressure agents, emulsifiers, demulsifiers, friction modifiers, anti-rust agents, corrosion inhibitors, viscosity improvers, dyes, and solvents to improve handleability which may include alkyl and/or aryl hydrocarbons. These additives may be present in various amounts depending on the needs of the final product.

The concentrate might contain 0.01 to 90% by weight of the PPD. The PPD may be present in a final product, blend or concentrate in (in a minor amount, i.e., up to 50% by weight) any amount effective to act as a pour point depressant but is preferably present in crude oils, residual oils, oil of lubricating viscosity, hydraulic oils, fuel oils or automatic transmission fluids in an amount of from about 0.0025 to about 4%, preferably 0.05 to about 2% by weight.

EXAMPLE 1

(All parts are parts by weight)

Naphthalene is mixed with seven parts of $CH_2Cl_2$ and 0.2 parts of $AlCl_3$. Chlorinated hydrocarbon (2.7 parts) is added slowly into the reaction mixture at 15° C. The reaction mixture is held for 5 hours at ambient temperature or until the release of HCl is complete. The mixture is then cooled to about 5° C. and 7.3 parts of an alpha olefin mixture is added over 2 hours while maintaining the temperature of the reaction mixture between 0° and 10° C.

The catalyst is decomposed by the careful addition of 0.8 parts 50% aqueous NaOH. The aqueous layer is separated and the organic layer is purged with $N_2$ and heated to 140° C. and 3 mm Hg to remove the volatiles. The residue is filtered to yield 97% of the theoretical yield weight of the product.

The present invention has been disclosed and described herein in what is believed to be its preferred embodiments. However, modifications will occur to those skilled in the art and such modifications are intended to be encompassed by the present invention.

We claim:

1. A mixture of compounds having the general structural formula (II):

$$Ar(R)-[Ar'(R')]_n-Ar'' \qquad (II)$$

wherein the Ar, Ar' and Ar'' are independently an aromatic moiety containing 1 to 3 aromatic rings and the mixture includes compounds wherein moieties are present with 0 substituents, 1 substituent, 2 substituents and 3 substituents, R and R' are independently an alkylene containing about 1 to 100 carbon atoms, and n is 0 to 1000, the composition being produced by a process comprising the steps of:
  (a) providing aromatic compounds containing 1 to 3 aromatic rings, which compounds include unsubstituted aromatics, monosubstituted aromatics, disubstituted aromatics and trisubstituted aromatics, the compounds being precursors for aromatic moieties Ar, Ar' and Ar'' in a reactor;
  (b) adding a FRIDEL-CRAFTS or Lewis Acid catalyst to the reactor;
  (c) adding a chlorinated hydrocarbon to the reactor;
  (d) adding an olefin to the reactor;
  (e) adding $CH_2Cl_2$ to the reactor wherein step (e) is carried out concurrently with or prior to at least one of steps (a–d).

2. The mixture as claimed in claim 1, wherein step (e) is carried out concurrently with or prior to step (c) or step (d).

3. The mixture as claimed in claim 1, wherein compounds are present in the mixture wherein their aromatic moieties are naphthalene, the olefin contains about 16 to 18 carbon atoms and the chlorinated hydrocarbon contains about 20 to 26 carbon atoms.

4. The mixture as claimed in claim 1, wherein the catalyst is $AlCl_3$, step (c) is carried out prior to step (d) and the container contents are cooled after step (c) and prior to step (d) to a temperature of about 0° C. to about 5° C. and the olefin is slowly added so as to maintain the temperature at about 0° C. to about 5° C. during the addition of the olefin.

5. The mixture as claimed in any of claims 1, 2, 3, or 4, further comprising the steps of:
  deactivating the catalyst after completing steps (a)–(e);
  neutralizing;
  heating to a temperature in the range of about 50° C. to about 130° C. to remove volatile components; and
  filtering and recovering the mixture of compounds therein which have the general structural formula (II).

6. The mixture as claimed in claim 1 including compounds having a molecular weight ranging from about 300 to about 2,000.

7. The mixture as claimed in claim 4 including compounds having a molecular weight ranging from about 500 to about 10,000.

8. The mixture as claimed in claim 5 including compounds having a molecular weight ranging from about 271 to about 300,000.

9. A concentrate comprising from about 0.1 to about 90% by weight of the mixture produced by the process as claimed in any one of claims 1, 2, 3, 4 or 5.

10. A concentrate as claimed in claim 9 wherein the concentrate includes an additive selected from the group consisting of dispersants, detergents, antioxidants, antiwear agents, extreme pressure agents, emulsifiers, demulsifiers, friction modifiers, anti-rust agents, corrosion inhibitors, viscosity improvers, dyes and solvents to improve handleability.

11. A hydrocarbon oil composition comprising a major portion of a distillate petroleum fraction and from about 0.0025 to about 4 weight percent of a composition produced by the process as claimed in claim 5.

12. A fuel oil composition comprising a major portion of a distillate petroleum fraction having an atmospheric boiling range of from about 120° C. to about 400° C. and from about 0.0025 to about 4 weight percent of the mixture produced by the process as claimed in claim 5.

13. A crude oil composition comprising a major portion of a natural crude oil and about 0.0025 to about 4 weight percent of the mixture produced by the process as claimed in claim 5.

14. A lubricating composition comprising a major amount of a oil of lubricating viscosity and about 0.0025 to about 4 weight percent of the mixture produced by the process as claimed in claim 5.

15. A lubricating composition as claimed in claim 14, wherein the oil is a hydrocarbon oil.

16. A lubricating composition as claimed in claim 14, wherein the oil is a synthetic fluid.

17. A lubricating composition as claimed in claim 14, wherein the oil is an automatic transmission fluid.

18. A lubricating composition as claimed in claim 14, wherein the oil is a gear lubricant.

* * * * *